United States Patent [19]

Kropp et al.

[11] 3,980,633
[45] Sept. 14, 1976

[54] 4-AMINO PYRIDAZINIUM COMPOUNDS HAVING PHARMACALOGICAL PROPERTIES

[75] Inventors: Rudolf Kropp, Limburgerhof; Franz Reicheneder; August Amann, both of Ludwigshafen; Hubert Giertz, Limburgerhof, all of Germany

[73] Assignee: BASF Aktiengesellschaft, Ludwigshafen (Rhine), Germany

[22] Filed: Sept. 12, 1973

[21] Appl. No.: 396,615

[30] Foreign Application Priority Data
Sept. 15, 1972 Germany............................ 2245248

[52] U.S. Cl..................... 260/250 A; 260/247.5 D; 260/250 AH; 424/248; 424/250; 260/247.1 E; 260/247.2 R; 424/232
[51] Int. Cl.$^2$............. C07D 237/20; C07D 403/04; C07D 413/04
[58] Field of Search... 260/250 A, 250 AH, 247.5 D

[56] References Cited
UNITED STATES PATENTS

| | | | |
|---|---|---|---|
| 3,510,488 | 5/1970 | Kremer et al................. | 260/250 A |
| 3,631,038 | 12/1971 | Reicheneder et al.......... | 260/250 A |
| 3,671,525 | 6/1972 | Reicheneder et al.......... | 260/250 A |

FOREIGN PATENTS OR APPLICATIONS

| | | | |
|---|---|---|---|
| 2,003,461 | 8/1971 | Germany...................... | 260/250 A |

OTHER PUBLICATIONS

Reicheneder, et al., Chemical Abstract 78:115221a of Ger. Offen. 2,139,687, dated Feb. 15, 1973.

*Primary Examiner*—Alton D. Rollins
*Assistant Examiner*—Mark L. Berch
*Attorney, Agent, or Firm*—Johnston, Keil, Thompson & Shurtleff

[57] ABSTRACT

New pyridazinium compounds which can be used as intermediates and are of interest because of their pharmacological properties, and their production.

The invention relates to new pyridazinium compounds and their production. These compounds are of pharmacological interest.

In DOS No. 1,912,941 6-alkoxypyridazinium compounds are said to have valuable pharmacological properties. Furthermore pyridazinium compounds are known for example as starting materials for pesticides and dyes from DOS No. 2,003,461 or U.S. Patent 3,510,488.

The quaternization of pyridazines into pyridazinium compounds is described in an article in Acta. Chem. Scand., 21 (1967), 1067 to 1080, and the reaction of 6-chloropyridazinium compounds with amines is described in volume 23 (1969), 2534 to 2536.

3 Claims, No Drawings

4-AMINO PYRIDAZINIUM COMPOUNDS HAVING PHARMACALOGICAL PROPERTIES

The present invention provides novel pyridazinium compounds of the general formula:

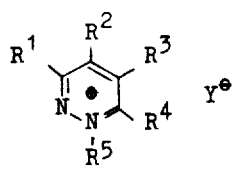 (1)

in which
R$^1$ is hydrogen, halogen, alkyl of one to five carbon atoms, phenyl or

in which one R$^7$ may be the same as or different from the other R$^7$ and each is hydrogen, hydroxyl, methoxy, alkyl of one to twelve carbon atoms, cyclohexyl, benzyl, or unsubstituted or substituted phenyl, or one R$^7$ together with the other R$^7$ is tetramethylene, pentamethylene or 3-oxatetramethylene;

R$^2$ is halogen, hydroxyl, alkoxy of one to eight carbon atoms, phenoxy, —SR$^6$ in which R$^6$ is alkyl of one to twelve carbon atoms, cyclohexyl, benzyl, unsubstituted or substituted phenyl,

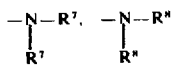

in which one R$^8$ is identical with or different from the other R$^8$ and each is hydrogen, alkyl of one to three carbon atoms, unsubstituted or substituted phenyl, cyclohexyl, benzyl, or —NHSO$_2$R$^9$ in which R$^9$ is phenyl, p-toluyl or p-anilino;

R$^3$ is hydrogen, halogen, alkyl of one to four carbon atoms, alkoxy of one to four carbon atoms, phenoxy or

R$^4$ is hydrogen, alkoxy —OR$^{10}$ in which R$^{10}$ is alkyl of five to 10 carbon atoms, aralkyl of seven to ten carbon atoms, unsubstituted or substituted phenyl, cycloalkyl of five to eight carbon atoms in the ring, hydroxyl, mercapto, —SR$^6$,

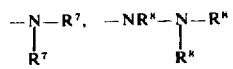

or —NHSO$_2$R$^9$; and

R$^5$ is alkyl of one to twelve carbon atoms, cycloalkyl of five to eight carbon atoms in the ring, unsubstituted or substituted phenyl, or aralkyl of seven to ten carbon atoms; and Y$^-$ is an anion.

Y$^-$ may be the anion of an inorganic acid such as perchloric acid, hydrochloric acid, hydrobromic acid, hydroiodic acid, phosphoric acid, carbonic acid, sulfuric acid, methylsulfuric acid, ethylsulfuric acid, trifluoromethylsulfonic acid, nitric acid or fluoboric acid, or an organic acid such as formic acid, acetic acid, trifluoroacetic acid, propionic acid, glycolic acid, lactic acid, pyruvic acid, oxalic acid, malonic acid, succinic acid, maleic acid, fumaric acid, malic acid, tartaric acid, citric acid, ascorbic acid, benzoic acid, phenylacetic acid, 4-aminobenzoic acid, 4-hydroxybenzoic acid, anthranilic acid, cinnamic acid, mandelic acid, salicylic acid, 4-aminosalicylic acid, 2-acetoxysalicylic acid, p-toluenesulfonic acid, isonicotinic acid, nicotinic acid, methionine, tryptophan, lysine and arginine.

Preferred anions are those of fluoboric acid, p-toluenesulfonic acid, hydrobromic acid and acetic acid and particularly preferred anions are those of perchloric acid, sulfuric acid, hydrochloric acid, methylsulfuric acid and trifluoromethylsulfuric acid.

Specific examples of R$^1$ are:
chloro, methyl, ethyl, phenyl, amino, methylamino, dimethylamino, bynzylamino, anilino, p-toluidino, pyrrolidino, piperidino and morpholino.

The preferred R$^1$ is hydrogen.

Examples of R$^2$ are:
chloro, methoxy, ethoxy, butoxy, phenoxy, methylmercapto, ethylmercapto, laurylmercapto, benzylmercapto, phenylmercapto, amino, methylamino, dimethylamino, ethylamino, β-chloroethylamino, isopropylamino, γ-methoxypropylamino, pentylamino, dodecylamino, benzylamino, cyclohexylamino, anilino, p-toluidino, m-chloroanilino, m-trifluoroanilino, pyrrolidino and toluenesulfonamido.

Preferred examples for R$^2$ are:
alkoxy of one to eight carbon atoms and particularly of one to four carbon atoms or the radical

in which one R$^7$ is identical with or different from the other R$^7$ and is hydrogen, unsubstituted or substituted alkyl of one to three carbon atoms and cyclohexyl. Suitable substituents for alkyl radicals R$^7$ are particularly chloro, methoxy, ethoxy, phenyl and phenyl bearing chloro, methyl or trifluoromethyl as substituent.

Examples of R$^3$ are:
chloro, bromo, methyl, methoxy, ethoxy, phenoxy, methylamino and dimethylamino.

Hydrogen and chloro are preferred for R$^3$.

Examples of R$^4$ are:
pentoxy, octoxy, cyclohexyloxy, phenoxy, methylmercapto, ethylmercapto, dodecylmercapto, β,γ,γ-trichloroallylmercapto, β-dimethylaminoethylmercapto, benzylmercapto, phenylmercapto, dimethylamino, isopropylamino, n-butylamino, anilino, benzylamino, phenylethylamino, pyrrolidino, piperidino, morpholino, hydrazino, methylhydrazino, phenylhydrazino and p-toluenesulfonamido.

Preferred examples of R$^4$ are:
hydrogen, —OR$^{10}$ where R$^{10}$ is alkyl of five to 10 carbon atoms, phenyl, phenyl bearing chloro or methyl as a substituent, —SR$^6$ where R$^6$ is alkyl of one to 12 carbon atoms which may bear chloro or dialkylamino (with a lower alkyl) as substituents, benzyl or phenyl, or

where one $R^{11}$ is the same as or different from the other $R^{11}$ and each is hydrogen, alkyl of one to six and particularly of one to four carbon atoms which may bear phenyl as a substituent, or phenyl or one $R^{11}$ together with the other $R^{11}$ is tetramethylene, pentamethylene or 3-oxatetramethylene, or

in which $R^{12}$ is hydrogen or lower alkyl and particularly methyl.

Examples of $R^5$ are:
methyl, ethyl, β-hydroxyethyl, γ-methyoxypropyl, dodecyl, cyclopentyl, cyclohexyl, cyclooctyl, phenyl, p-chlorophenyl, tolyl, m-trifluorophenyl and benzyl.

Preferred examples of $R^5$ are phenyl which may bear as substituents: chloro, lower alkyl and particularly methyl, trifluoromethyl, benzyl, lower alkyl and particularly methyl and cycloalkyl of five to eight carbon atoms in the ring.

The meaning particularly preferred for $R^2$ is $NH_2$.

The meaning particularly preferred for $R^3$ is hydrogen.

The meanings particularly preferred for $R^4$ are hydrogen, alkylthio with a lower alkyl particularly methyl or ethyl, pyrrolidino and dialkylamino with a lower alkyl.

The meaning particularly preferred for $R^5$ is phenyl.

The new compounds may be prepared by various methods known per se.

a. Pyridazinium compounds of the formula (1) according to the invention in which $R^4$ is hydrogen may be prepared from pyridazinium compounds halogenated in the 6-position and having the formula (2):

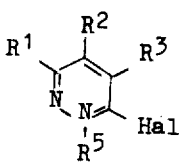

in which $R^1$ is hydrogen and $R^2$ is

having the meanings stated to be preferred, $R^3$ has the preferred meanings and Hal is chloro or bromo, by replacing the halogen in the 6-position by hydrogen in the presence of a catalyst and if desired in the presence of an agent binding hydrogen halide in a solvent or suspension agent.

b. Pyridazinium compound of the formula (1) in which $R^4$ is hydrogen may be prepared from starting compounds of the formula (3):

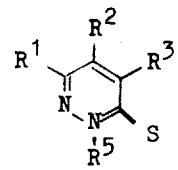

in which $R^1$ is hydrogen, $R^2$ is

with the preferred meanings, $R^3$ is hydrogen or chloro and $R^5$ has the preferred meanings by reaction with hydrogen peroxide in an organic acid as solvent.

c. Pyridazinium compounds of the formula (1) in which $R^4$ is hydrogen and $R^2$ is alkoxy of one to eight carbon atoms may be prepared from starting compounds of the formula (4):

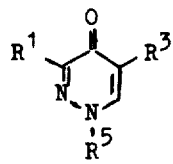

in which $R^1$ is hydrogen, $R^3$ is hydrogen or halogen and particularly chloro or bromo, and $R^5$ has the preferred meanings by alkylating by a conventional method the keto group in the 4-position.

d. Pyridazinium compounds of the formula (1) in which $R^4$ is hydrogen, $R^1$, $R^2$ and $R^3$ are each chloro and $R^5$ is alkyl of one to twelve carbon atoms may be prepared for example from starting compounds of the formula (5):

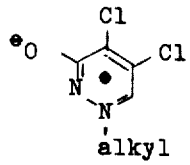

by replacing the oxygen by chlorine.

e. Pyridazinium compounds of the formula (1) in which $R^4$ is hydrogen, $R^1$, $R^3$ and $R^5$ have the meanings given above and $R^2$ is a radical attached to the pyridazinium ring system by way of an oxygen, sulfur or nitrogen atom may be prepared from starting compounds of the formula (6):

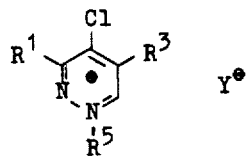

by reacting the compound (6) with an oxygen, sulfur or nitrogen compound bearing a hydrogen atom on said hetero atom and bearing $R^2$ as a substituent so that hydrogen chloride is eliminated.

Pyridazinium compounds of the formula (1) with hydrogen in the 6-position ($R^4$ = H) are obtained as a preferred group by the methods described under (a) to (e).

f. Compounds of the general formula (1) in which $R^4$ is OH or SH may be obtained for example by treating a compound of the formula (7):

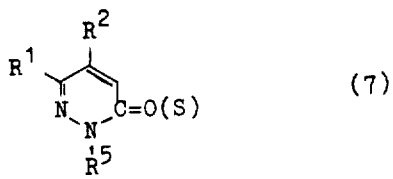

with a strong proton acid.

g. Compounds of the formula (1) in which $R^1$ and $R^3$ each is hydrogen and $R^4$ is alkoxy with an alkyl of five to ten carbon atoms may be prepared from starting compounds of the formula (8):

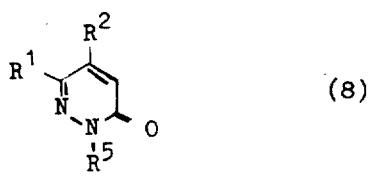

in which $R^1$ is hydrogen and $R^2$ and $R^5$ have the preferred meanings by alkylating the keto group in the 6-position with a sulfonic ester of five to 10 carbon atoms in the ester alcohol by a conventional method.

h. Compounds of the formula (1) in which $R^1$ and $R^3$ are both hydrogen and $R^4$ is $OR^{10}$ with the above meanings may also be prepared from starting compounds of the formula (9):

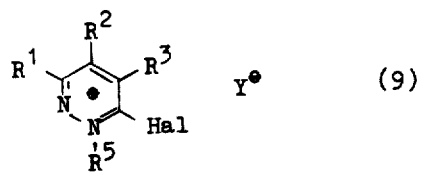

in which $R^1$ and $R^3$ are both hydrogen, $R^2$ is

with the above preferred meanings and $R^5$ has the above preferred meanings, Hal being chloro or bromo, by reaction with an alcohol of five to ten carbon atoms or a phenol in the presence of an agent which binds hydrogen chloride or by reaction with a corresponding alcoholate or phenolate.

$h_1$. Another method of preparing compounds of the formula (1) in which $R^3$ is hydrogen and $R^4$ is alkoxy having an alkyl of five to 10 carbon atoms is by reaction of a starting compound of the formula (10):

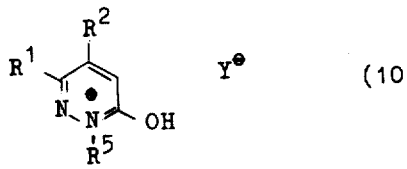

with an alcohol or alkyl halide of an alkyl of five to 10 carbon atoms. In the formula (10) $R^1$, $R^2$ and $R^5$ have the meanings given above. When carrying out etherification $R^2$ should conveniently not be OH.

Pyridazinium compounds having alkoxy of five to ten carbon atoms in the 6-position may be prepared as a preferred group of compounds of the formula (1) by the methods specified under (g), (h) and ($h_1$).

i. Compounds of the formula (1) in which $R^1$ is hydrogen, $R^3$ is hydrogen or chloro and $R^4$ is $SR^6$ where $R^6$ is unsubstituted or substituted alkyl of one to 12 carbon atoms may be prepared from starting compounds of the formula (11):

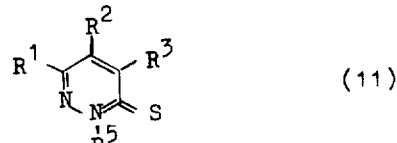

in which $R^1$ is hydrogen, $R^3$ is hydrogen or chloro and $R^2$ and $R^5$ have the preferred meanings given above by alkylating the sulfur in the 6-position by a conventional method.

j. Compounds of the formula (1) in which $R^1$ and $R^3$ are both hydrogen and $R^4$ is $SR^6$ where $R^6$ is unsubstituted or substituted alkyl of one to 12 carbon atoms or phenyl may be obtained from compounds of the formula (12):

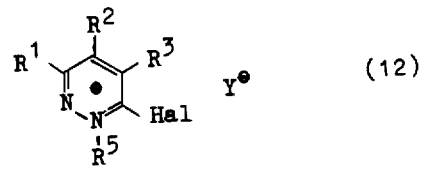

in which $R^1$ and $R^3$ are both hydrogen, $R^2$ is

having the above preferred meaning and $R^5$ has the above preferred meaning, and Hal is chloro or bromo, by reaction with a thioalcohol of one to twelve carbon atoms or thiophenol in the presence of an agent which binds hydrogen chloride or by reaction with the appropriate sodium or potassium mercaptide or a thiophenolate.

$j_1$. The same compounds of formula (1) with $R^4 = SR^6$ may be obtained from compounds of the formula (13):

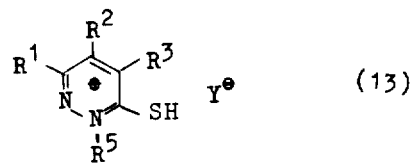

by reaction with an alkyl halide.

Pyridazinium compounds having the radical $SR^6$ in the 6-position can be prepared as a preferred group of compounds of the formula (1) by the methods specified under (i), (j) and ($j_1$).

k. Compounds of the formula (1) in which $R^4$ is

with the above preferred meanings or

with the above preferred meanings may be prepared from starting compounds of the formula (14):

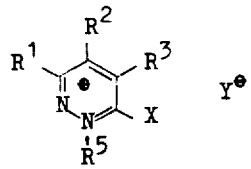

in which $R^1$ is hydrogen, $R^3$ is hydrogen or chloro, $R^2$ is

with the preferred specified meanings, $R^5$ has the preferred specified meanings and X is halogen, particularly chloro or bromo, -O-alkyl or -S-alkyl particularly of one to four carbon atoms in the alkyl radical, by replacing the substituent X by reaction with ammonia, if desired in the form of urea, or an amine or hydrazine substituted in the manner specified, if desired in a solvent, at elevated temperature.

l. Compounds of the formula (1) in which $R^4$ is $-NHSO_2R^9$ may be prepared by reacting a starting compound of the formula (15):

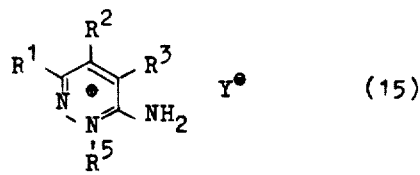

with a compound of the formula $Cl-SO_2R^9$ in which $R^9$ has the above meaning. For an advantageous process $R^2$ should not be OH and, if one of the radicals is

$R^7$ should not be —H or —OH.

Pyridazinium compounds having a substituted amino radical in the 6-position may be prepared as a preferred group of compounds of formula (1) by the methods specified under (k) and (l).

m. Compounds of the formula (1) in which $R^3$ is hydrogen and $R^4$ is hydrogen or

with $R^{11}$ having the said meanings may be prepared from starting compounds of the formula (16):

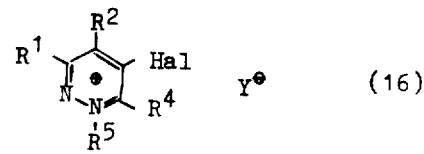

in which $R^1$ is hydrogen, $R^2$ is

with the above preferred meaning, $R^4$ is hydrogen,

chloro or bromo, $R^5$ has the above preferred meanings and Hal is hydrogen, chloro or bromo, by replacing the halogen by hydrogen in the presence of a catalyst and if desired in the presence of an agent which binds hydrogen halide in a solvent or suspension agent at elevated temperature, particularly at from 50° to 120°C, with or without the use of superatmospheric pressure.

Convenient measures to be taken in the individual methods and further explanations will now be described.

Regarding (a):

A very suitable dehalogenating agent is hydrogen in the presence of a catalyst such as Raney nickel, Raney cobalt, palladium, platinum, in the presence or absence of agents which bind hydrogen halides such as sodium bicarbonate, sodium hydroxide, calcium hydroxide, triethylamine or pyridine. The dehalogenation may be carried out at atmospheric pressure or at a pressure of up to 300 atmospheres gauge and at ambient or elevated temperature up to 120°C. The dehalogenation is carried out in an inert solvent or suspension agent such as water, an ether such as diethyl ether, tetrahydrofuran or dioxane, an ester such as ethyl acetate or butyl acetate, or a cyclic aliphatic or aromatic hydrocarbon such as benzene, toluene or cyclohexane. The reaction may be carried out in batches or with a stationary catalyst; it may be carried out continuously. Isolation of the reaction products is carried out after the catalyst has been separated, by filtration or concentration of the reaction mixture or precipitation of the pyridazinium salt as a sparingly soluble perchlorate by adding perchloric acid or sodium or potassium perchlorate.

The starting compound of formula (2) may be obtained by chlorination of a pyridazone by the method described in DOS No. 2,016,691. The starting compounds may also be obtained as described by H. Lundt and P. Lunde in Acta Chem. Scand., 21 (1967), 1067 to 1080 by quaternization of suitable substituted pyridazines.

Reactions specified under (m) may be carried out under analogous conditions.

Regarding (b):

The reaction takes place with hydrogen peroxide solution in an organic acid, preferably in glacial acetic acid as solvent at a temperature of from 40° to 150°C, preferably from 70° to 120°C. After the glacial acetic acid has been removed, the reaction product crystallizes out as the sulfate. As a rule 30% by weight hydrogen peroxide is used by less highly or more highly concentrated hydrogen peroxide may be used. At least three moles of hydrogen peroxide is necessary for the oxidation of sulfur; an excess of up to 500% is not detrimental. Instead of using glacial acetic acid as the solvent, other acids may be used such as trifluoroacetic acid or propionic acid. The reaction may be carried out at atmospheric or superatmospheric pressure. The reaction product, after the solvent has for the most part been distilled off, may be taken up in water and precipitated as the sparingly soluble perchlorate by introducing perchloric acid or sodium or potassium perchlorate.

Starting materials of the formula (3) may be prepared for example by the method described in Japanese published application No. 6067/67 by reaction of a pyridazone-(6) with phosphorus pentasulfide. It may also be obtained according to DOS 1,670,309 from a 6-halopyridazonimine-(4) by reaction for example with hydrogen sulfide.

Regarding (c):

The alkylation which is combined with a quaternization may be carried out with oxonium salts such as triethyloxonium fluoborate in an inert solvent, for example toluene, methylene chloride, acetone, acetonitrile, at elevated temperature of from 50° to 150°C, preferably from 80° to 130°C, at atmospheric or superatmospheric pressure. When using other alkylating agents such as dialkyl sulfate, benzyl chloride or sulfonic esters, it is possible to omit the solvent.

The starting compounds of the formula (4) may be obtained for example according to J. Druey, Helv. Chim. Acta, 39 (1956), 1755.

Regarding (d):

Chlorination is carried out with a halogen-transferring agent such as phosgene, thionyl chloride, phosphorus oxychloride, phosphorus pentachloride or oxalkyl chloride in the chlorinating agent itself or in an inert solvent such as chlorohydrocarbon or benzene at temperatures of from 20° to 100°C.

Starting compounds of the formula (5) are obtained for example by the method described in DOS No. 2,003,461.

Corresponding compounds specified under (c) can be chlorinated under the same conditions.

Regarding (e):

The reaction of 4-halopyridazinium salts with the appropriate reactants is carried out in solution or suspension in an inert solvent, for example acetonitrile, or in an excess of reactants as a solvent or in a solution of the same, if necessary with the addition of a base which binds hydrogen halide such as pyridine, triethylamine, caustic soda solution, calcium hydroxide, sodium carbonate solution and the like, and while heating to a temperature of from 40° to 170°C and preferably from 70° to 120°C.

Starting compounds of the formula (6) may be obtained as described under (c) or (d).

Regarding (f):

The treatment of the starting compounds (7) (which are accessible in conventional manner according to K. Dury, Angew. Chemie, 77 (1965), 285) with strong acids such as perchloric acid, sulfuric acid, hydrohalic acids, phosphoric acid, trifluoroacetic acid, methanesulfonic acid or toluenesulfonic acid is carried out by adding the acid or a substance which forms the acid, as for example an acid chloride to the solution or suspension of the starting compound, for example in water, alcohol, acetonitrile, benzene or carbon tetrachloride at a temperature of from 10° to 150°C and preferably at from 20° to 80°C.

Regarding (g):

Alkylation of starting compounds of the formula (8) is carried out analogously to the method of DOS No. 1,912,941 in which the production of the appropriate starting materials is also given.

Regarding (h), (j) and (k):

For the reaction for exchanging substituents in the 6-position of the pyridazinium compound with alcohols or alcoholates, mercaptans, amines and hydrazines, the starting compound is dissolved or suspended in an inert solvent, for example acetonitrile, or in an excess of reactant or solution of the same, a base which binds hydrogen halide such as pyridine, triethylamine, caustic soda solution, calcium hydroxide or sodium carbonate solution is added if necessary and the whole is heated to a temperature of from 40° to 170°C and preferably from 70° to 120°C. Introduction of the amino group may be achieved particularly advantageously by a urea melt. When alcoholates are being used, alkali metal or alkaline earth metal alcoholates such as sodium, potassium or magnesium alcoholates, or also aluminum alcoholates are convenient.

Regarding ($h_1$):

The reaction is carried out by heating the reactants with or without adding an inert solvent to a temperature of up to 250°C at atmospheric or superatmospheric pressure, with or without the addition of an agent which eliminates water.

Regarding ($j_1$):

The reaction may be carried out by heating the two reactants while stirring at from 80° to 130°C dissolved or suspended, if desired in an inert solvent such as benzene or xylene.

Regarding (i):

Quaternization can be carried out by suspending or dissolving the compound in the alkylating agent or in an inert solvent such as methylene chloride, perchloroethylene, benzene, xylene, dioxane, tetrahydrofuran or acetone adding the alkylating agent such as methyl iodide, benzyl chloride, dimethyl sulfate, tosyl octyl ester or oxonium salt and heating at a temperature of from 30° to 170°C and preferably from 80° to 130°C.

As a rule 1 mole of alkylating agent is used per mole of pyridazinethione; an excess of up to 2000% is not detrimental. The reaction product is thrown down as an insoluble substance when hydrocarbons and chlorohydrocarbons are used. If the alkylating agent, for example dimethyl sulfate, is used as solvent, the reaction product crystallizes out upon cooling. It may be recovered for example by filtration. It may however also be extracted from the reaction mixture with water and recovered from the aqueous solution for example by evaporating the aqueous solution and/or adding perchloric acid or sodium perchlorate so that the sparingly soluble perchlorate is precipitated. Other salts may be prepared in an analogous manner. Sometimes the reaction product remains dissolved, for example when dioxane is used as solvent or in the case of certain alkylating agents, as for example tosyl esters.

The production of 6-alkyl- or phen-thio-pyridazinium salts by reaction of the 6-halo compound with a mercaptan according to procedure (i) is carried out as a rule by dissolving or suspending the 6-halopyridazinium salt in an inert solvent, for example acetonitrile, adding the equivalent amount of mercaptan and then the agent for binding hydrogen chloride, for example triethylamine, and stirring for half an hour to 5 hours at about 80°C. The reaction product can be either immediately suction filtered or recovered by concentration of the reaction mixture and adding water to the residue, if desired with perchloric acid. Water may itself also be used as solvent for the reaction.

Regarding (k):

Reaction with nitrogen compounds is carried out analogously to the procedure described under (j). The special method of substituting the $NH_2$ group by means of a urea melt is carried out by melting about ten times the amount of urea and introducing the 6-halopyridazinium salt into the melt at from 130° to 140°C and cooling after from 10 to 100 minutes. The reaction product can be recovered by dissolving the reaction mixture in water and isolating the pyridazinium salt as the perchlorate or in the case of an $NH_2$ group in the 4-position precipitating the reaction product by means of dilute caustic soda solution as a water-insoluble neutral product and converting this in a second stage into the actual pyridazinium salt by treatment with an acid.

Regarding (l):

In this method the 6-aminopyridazinium salt is reacted with a sulfonyl chloride in substance, if desired with the addition of an agent for binding halogen, or in an inert solvent at a temperature of from 50° to 200°C and preferably from 60° to 150°C. A solvent may also be chosen which is itself capable of binding hydrogen halide, for example acetamide or dimethylformamide.

The starting compounds are prepared by the methods described under (k).

Compounds according to the invention in which $R^2$ is preferably an amino group or one of the secondary amino groups having the said meanings, can be converted by conventional methods into the bases corresponding thereto.

The new pyridazinium compounds have valuable pharmacological properties. On test animals they have the effects in peroral and intravenous administration of a prolonged increase in blood pressure, of showing a reserpin antagonism and an antidepressive or anti-Parkinson effect and are capable of increasing excretion of urine in rats. The antidepressive effect can be shown experimentally by suppression of lid paralysis in rats or mice induced by tetrabenazine and serpasil, an increase in the noradrenalin action in decapitated animals, a lowering of the body temperature and so on. Some members of the above class of compounds have also been found experimentally to be analgesic and antiinflammatory and to inhibit tremor induced by tremorine and physostigmine.

The new pyridazinium compounds when administered intravenously narcotized rats and cats cause powerful and prolonged increase in blood pressure in doses of from 0.1 to 1 mg/kg. The noradrenalin pressor effect in pithed rats is considerably increased by this dosage. The circulatory effects can be detected particularly clearly in the case of 1-phenyl-4-amino-6-methyl(and ethyl)mercaptopyridazinium methosulfate (or hydrogen sulfate). In the case of these compounds increased diuresis occurs after 50 mg/kg p.o. The substances also show central stimulating effects in mice when administered perorally, the effects being so marked in the case of 1-phenyl-4-aminopyridazinium perchlorate and 1-p-chlorophenyl-4-aminopyridazinium perchlorate that fatality increased by aggregation is to be observed at 46 mg/kg.

An antireserpin or antitetrabenazine effect can be demonstrated at a dosage of up to 10 mg/kg p.o. in mice in the case of the new pyridazinium compounds except 1-phenyl-4-amino-5-chloro-6-anilinopyridazinium chloride, because both ptosis and motility inhibition are suppressed. In the case of some of the pyridazinium compounds there are also analgesic and antiinflammatory effects.

The effects on the circulation in cats (Table 1), the effects on reserpin-induced ptosis in mice (Table 2) and neuropharmacological effects in mice (Tables 3 to 6) are collected in the following Tables for some of the pyridazinium compounds. Comparative investigations of some pyridazinium derivatives on the circulation of cats (Table 1).

Method:

Cats of both sexes in the weight range from 1.3 to 3.7 kg are narcotized with hexobarbital sodium (EVIPAN-SODIUM — registered Trade Mark) at 200 mg/ks s.c., further narcotic being given if necessary. The animals breathe spontaneously. Pressure measurement is carried out by way of a Statham P23Db-recorder in the A. femoralis.

The pulse frequency is determined by means of a ratemeter (Eka-Puls., Messrs. HSE, Hugstetten, Germany) as a peak-to-peak integration from the R-R distance of the ECG. Peripheral flow is determined electromagnetically (Statham, Multiflow, m 4000) externally on the femoralis in the vicinity of the inguinal ligament.

The injection of the substances takes place in increasing dosage (three doses per animal) into a V. saphena.

Solvent: physiological common salt solution.

Concentration: $10^{-3}$.

Table 1

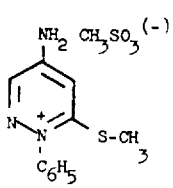

| Substance | Dose mg/kg | TA | n | | Art. pressure (Min Hg) | | | | Pulse frequency (pulse/min) | | | | Peripheral flow ml/min | | | |
|---|---|---|---|---|---|---|---|---|---|---|---|---|---|---|---|---|
| | | | | | SV | EV | %D | Dur | SV | EV | %D | Dur | SV | EV | %D | Dur |
| | 0.1 | i.v. | 4 | $\bar{x}$ | 118 | 141 | +20 | 16 | 123 | 197 | +8 | 15 | 3.8 | 4.7 | +22.5 | 6.5 |
| | | | | $s\bar{x}$ | 13 | 14 | 2.7 | 4.8 | 22 | 24 | 1.4 | 5 | 1.2 | 1.5 | 0.5 | 1.5 |
| | 0.464 | i.v. | 4 | $\bar{x}$ | 82 | 116 | +43 | 59 | 146 | 166 | +14 | 43 | 8.5 | 10.5 | +22 | 8 |
| | | | | $s\bar{x}$ | 11 | 13 | 4.3 | 15 | 18 | 19 | 1.6 | 14 | 1.8 | 2.5 | 2.8 | 3.5 |
| | 1.0 | i.v. | 5 | $\bar{x}$ | 91 | 138 | +52 | 108 | 145 | 173 | +20 | 97 | 8.3 | 10.7 | +33 | 6 |
| | | | | $s\bar{x}$ | 9 | 17 | 17 | 36 | 15 | 13 | 5.0 | 39 | 1.6 | 1.5 | 16 | 2.8 |

Table 1-continued

| Substance | Dose mg/kg | TA | n | | Art. pressure (Min Hg) SV | EV | %D | Dur | Pulse frequency (pulse/min) SV | EV | %D | Dur | Peripheral flow ml/min SV | EV | %D | Dur |
|---|---|---|---|---|---|---|---|---|---|---|---|---|---|---|---|---|
| [structure: 4-amino-1-phenylpyridazinium ClO4−] | 0.1 | i.v. | 4 | x̄ | 93 | 110 | +20 | 65 | 171 | 228 | +36 | 68 | | | | |
| | | | | sx̄ | 6 | 7 | 11 | 27 | 22 | 33 | 15 | 26 | | not measured | | |
| | 0.215 | i.v. | 4 | x̄ | 83 | 120 | +37 | 28 | 219 | 256 | +18 | 32 | | | | |
| | | | | sx̄ | 4.2 | 13 | 17 | 8 | 30 | 31 | 9.7 | 8 | | | | |
| | 0.464 | i.v. | 3 | x̄ | 81 | 129 | +77 | 108 | 164 | 131 | +12 | 62 | | | | |
| | | | | sx̄ | 13 | 13 | 52 | 67 | 20 | 11 | 8 | 39 | | | | |
| [structure: 4-amino-1-phenyl-6-pyrrolidinyl-pyridazinium ClO4−] | 0.464 | i.v. | 6 | x̄ | 91 | 130 | +44 | 142 | 148 | 178 | +22 | 137 | 8.9 | 7.0 | −21 | 33 |
| | | | | sx̄ | 7.7 | 9.1 | 5.4 | 11 | 13.8 | 13.4 | 3.9 | 11.7 | 2.9 | 2.0 | 12 | 28 |
| | 1.0 | i.v. | 6 | x̄ | 104 | 130 | +27 | 46 | 168 | 185 | +11 | 18 | 12.6 | 7.9 | −35 | 10 |
| | | | | sx̄ | 8 | 6.4 | 6 | 11 | 12 | 11.6 | 2 | 8.7 | 0.95 | 1.9 | 17 | 5 |
| | 2.15 | i.v. | 5 | x̄ | 105 | 126 | +20 | 39 | 181 | 186 | +3 | 19 | 15.4 | 12.2 | −18 | 24 |
| | | | | sx̄ | 6.7 | 6.7 | 3.7 | 7 | 13 | 12 | 3 | 3 | 3.5 | 0.45 | 16 | 21 |
| [structure: 4-amino-6-dimethylamino-1-phenylpyridazinium ClO4−] | 0.464 | i.v. | 4 | x̄ | 97 | 122 | +26 | 65 | 174 | 201 | +17 | 46 | 12.6 | 10.5 | −17 | 13 |
| | | | | sx̄ | 4.7 | 5.7 | 5.8 | 20 | 11.1 | 8.7 | 3.6 | 19.7 | 1.9 | 1.7 | 1 | 3 |
| | 1.0 | i.v. | 4 | x̄ | 109 | 131 | +21 | 38 | 182 | 192 | +6 | 27 | 13.5 | 19 | +50 | 7.5 |
| | | | | sx̄ | 5.5 | 6.3 | 4 | 6 | 12 | 13 | 5.8 | 12 | 2.8 | 1 | 39 | 2.5 |
| | 2.15 | i.v. | 4 | x̄ | 112 | 139 | +26 | 43 | 175 | 192 | +10 | 16 | 13.9 | 22.3 | +60.5 | 12 |
| | | | | sx̄ | 6.4 | 3 | 5 | 14 | 15 | 13 | 1.9 | 5.5 | 3.2 | 4.7 | 4.5 | 1 |

TA = type of administration;
SV = starting value;
EV = extreme value;
%D = percentage deviation;
Dur = duration in minutes Table 2

Reserpin antagonism in reserpin ptosis in mice.
The substances are administered per os at the same time as the reserpin (5 mg/kg s.c.)

| Substance | Dose (mg/kg) 0.1 | 0.215 | 0.464 | 1.0 | Inhibition of ptosis (x/n) 2.15 | 4.64 | 10.0 | 21.5 | 46.4 |
|---|---|---|---|---|---|---|---|---|---|
| [structure: 4-amino-6-methylthio-1-phenylpyridazinium CH3SO4−] | | | | 1/10 | 4/10 | | 7/10 | | 10/10 |
| [structure: 4-amino-1-phenylpyridazinium ClO4−] | 0/10 | 4/10 | 4/10 | 10/10 | | | | | |
| [structure: 4-amino-1-phenyl-6-pyrrolidinyl-pyridazinium] | | | 0/10 | 3/10 | 5/10 | 6/10 | 8/10 | | |

Table 2-continued

Reserpin antagonism in reserpin ptosis in mice.
The substances are administered per os at the same time as the reserpin (5 mg/kg s.c.)

| Substance | Dose (mg/kg) | | | | | Inhibition of ptosis (x/n) | | | |
|---|---|---|---|---|---|---|---|---|---|
| | 0.1 | 0.215 | 0.464 | 1.0 | 2.15 | 4.64 | 10.0 | 21.5 | 46.4 |

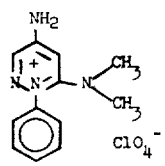

|  |  |  |  |  |  | 1/10 | 7/10 | 9/10 |

Table 3

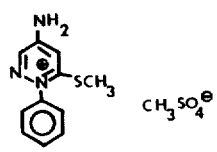

| Test | Dosage mg/kg | Result | | Remarks |
|---|---|---|---|---|
| Rotating rod | 100 | Animals which fall 0/10 | | in spite of stimulation with 46.4 mg/kg and sedation with 100 mg/kg there is no decrease in cooridination |
| | 215 | 0/10 | | |
| | | spasm inhibition | fatality in shock | No spasm inhibition; from |
| Electric shock | 0 | 0/10 | 2/10 | 21.5 mg/kg increased |
| | 10 | 0/10 | 3/10 | fatality in shock |
| | 21.5 | 0/10 | 5/10 | |
| | 46.4 | 0/10 | 9/10 | |
| | 100 | 0/10 | 9/10 | |
| | 215 | 0/10 | 9/10 | |
| Barbiturate sleep period | | sleep period | Prolongation of sleep | no prolongation of sleep up to 215 mg/kg |
| | 0 | 18.37 ± 1.60 | 0/8 | |
| | 46.4 | 17.07 ± 3.15 | 0/8 | |
| | 100 | 16.14 ± 2.52 | 0/8 | |
| | 215 | 21.18 ± 1.12 | 0/8 | |
| Toxicity | 215 | 0/10 | | |

Table 4

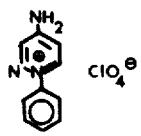

| Test | Dosage (mg/kg) | Result | | Remarks |
|---|---|---|---|---|
| Rotating rod | | Animals which fall (30 min. p.a.) | | Effect is short-lived, in spite of general symptoms up to 2 h p.a. no dosage-dependent decrease in coordination |
| | 10 | 5/30 | | |
| | 21.5 | 2/30 | | |
| | 46.4 | 5/30 | | |
| | | spasm inhibition | Fatality in shock | No spasm inhibition, from |
| Electric shock | 0 | 0/20 | 4/20 | 21.5 mg/kg increased |
| | 10 | 0/10 | 2/10 | fatality in shock |
| | 21.5 | 0/20 | 11/20 | |
| | 46.4 | 0/10 | 4/10 | |
| | 100 | 0/10 | 8/10 | |
| Barbiturate sleep period | | sleep period | Prolongation of sleep | Slight prolongation with 46.4 mg/kg |
| | 0 | 18.90 ± 3.85 | 0/8 | |

Table 4-continued

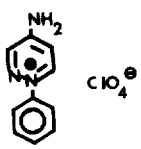

| Test | Dosage (mg/kg) | Result | | Remarks |
|---|---|---|---|---|
| | 10 | 16.71 ± 1.68 | 0/8 | |
| | 21.5 | 18.36 ± 3.11 | 0/8 | |
| | 46.4 | 30.23 ± 5.27 | 2/8 | |
| | | In isolation | | |
| Toxicity | 46.4 | 0/10 | | Fatality lower in isolation |
| | 100 | 0/10 | | than in aggregation |
| | | Aggregation | | |
| | 21.5 | 0/10 | | |
| | 46.4 | 1/10 | | |
| | 100 | 6/10 | | |

Table 5

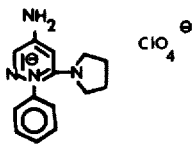

| Test | Dosage (mg/kg) | Result | | Remarks |
|---|---|---|---|---|
| Rotating rod | | Animals which fall (2ʰ p.a.) | | Effective from 60 minutes p.a. |
| | 46.4 | 1/10 | | Inhibition of coordination |
| | 100 | 0/10 | | with 215 mg/kg from 60 |
| | 215 | 7/9 | | minutes p.a. and fatality. |
| Electric shock | | Antispasmodic | Fatality in shock | No spasm inhibition |
| | 0 | 0/10 | 3/10 | |
| | 100 | 0/10 | 2/10 | |
| | 215 | 0/10 | 5/10 | |
| pentetrazole | 0 | 0/5 | 1/5 | No spasm inhibition. |
| spasm | 46.4 | 0/5 | 3/5 | Increased fatality in shock |
| | 100 | 0/5 | 4/5 | |
| | 215 | 0/4 | 3/4 | |
| barbiturate | | Sleep period | Prolongation of sleep time | No prolongation |
| sleep | 0 | 15.48 ± 3.43 | 1/8 | |
| | 46.4 | 16.37 ± 2.79 | 0/8 | |
| | 100 | 17.18 ± 4.34 | 1/8 | |
| | 215 | 15.08 ± 2.21 | 0/7 | |
| Toxicity | 100 | | 0/10 | |
| | 215 | | 9/10 | |

Table 6

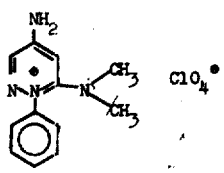

| Test | Dosage (mg/kg) | Result | | Remarks |
|---|---|---|---|---|
| Rotating rod | | Animals which fall (2ʰ p.a.) | | Effective from 120 minutes p.a. |
| | 46.4 | 1/10 | | Inhibition of coordination |
| | 100 | 0/10 | | and fatality with 215 mg/kg |
| | 215 | 4/9 | | from 2 hours a.p. |
| Electric shock | | Spasm inhibition | Fatality in shock | No spasm inhibition |

Table 6-continued

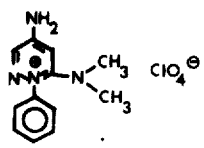

| Test | Dosage (mg/kg) | Result | | Remarks |
|---|---|---|---|---|
| | 0 | 0/10 | 2/10 | |
| | 46.4 | 0/10 | 1/10 | |
| | 100 | 0/10 | 0/10 | |
| | 215 | 0/10 | 5/10 | |
| Pentetrazole spasm | 0 | 0/10 | 2/10 | No spasm inhibition, increased fatality in shock |
| | 46.4 | 0/10 | 7/10 | |
| | 100 | 0/10 | 6/10 | |
| | 215 | 0/10 | 8/10 | |
| Barbiturate sleep period | | Sleep period | Prolongation of sleep period | Slight effect which 215 mg/kg |
| | 0 | 16.12 ± 3.00 | 0/8 | |
| | 46.4 | 16.62 ± 2.66 | 0/8 | |
| | 100 | 20.42 ± 3.76 | 1/8 | |
| | 215 | 34.21 ± 6.46 | 3/8 | |
| Toxicity | 100 | 0/10 | | |
| | 215 | 5/10 | | |

Explanation of Tables 3 to 6:
Material:
The investigations are carried out on female NMRI mice in the body weight range from 17 to 25 g. The test substances are administered orally; the volume administered is 10 ml/kg body weight. The substances of Tables 3 and 4 are in each case dissolved in water, those in Tables 5 and 6 are suspensions in 5% aqueous carboxymethylcellulose.

Methods:
a. Coordination test on the rotating rod:
At 30, 60, 120 and 240 minutes post applicationem (p.a.) the animals are registered which cannot keep their hold on the rod rotating at 10 rpm for two minutes (animals which fall).

b. Maximum electric shock:
The animals are shocked by way of aural electrodes at 30 and 120 minutes p.a.
Duration of shock: 0.2 second.
Frequency: 50 1/second.
Strength of shock: 20 milliamperes.
Sinus pulse.
The number of animals which do not react with a tonic streching spasm, and fatality in shock are determined.

c. Pentetrazole spasm:
Thirty minutes after administration of the test substance the animals receive 82.5 mg/kg of pentetrazole s.c. The number of animals which do not react with spasms within sixty minutes (spasm protection) and fatality in shock are determined during this period.

d. Barbiturate sleep period:
Thirty minutes after the test substance has been administered the animals receive an intravenous injection of hexobarbital (82.5 mg/kg). The sleep period determined is the time which elapses until reoccurrence of the reflex to rise, and under sleep prolongation there is given the number of animals having twice the sleep period of the controls.

e. Toxicity:
The number of animals which die within up to 24 hours p.a. is determined when groups of 10 animals are kept in cages and in one case when kept separate.

Evaluation:
In Tables 3 to 6 the number of reagents and the size of the group of animals or, where possible, the mean value and the mean error ($\bar{x} \pm s_{\bar{x}}$).

The new compounds are also important intermediates for dyes, photosensitizers, for growth regulators, for pesticides and for pharmaceutical products.

The following pyridazinum compounds of the general formula (1) are given by way of example:

1-phenyl-3,4-diaminopyridazinium perchlorate,
1-phenyl-4-dimethylamino-5-methylpyridazinium perchlorate,
1-cyclohexyl-4-isopropylamino-5-chloropyridazinium perchlorate,
1-phenyl-4-amino-5-bromopyridazinium perchlorate,
1-(p-chlorophenyl)-4-benzylamino-5-chloropyridazinium perchlorate,
1-phenyl-4-toluenesulfonamido-5-chloropyridazinium perchlorate,
1-phenyl-4-hydroxy-5-chloropyridazinium perchlorate,
1-phenyl-4ethylmercapto-5-chloropyridazinium perchlorate,
1-phenyl-4-phenoxy-5-chloropyridazinium perchlorate,
1-phenyl-4-amino-6-cyclohexyloxypyridazinium perchlorate,
1-phenyl-3-ethyl-4-chloro-5-methylamino-6-methylmercaptopyridazinium iodide,
1-phenyl-3,4-bis-(dimethylamino-6-methylmercaptopyridazinium perchlorate,
1-phenyl-4-amino-6-(p-toluene)-sulfonamidopyridazinium perchlorate,
1-phenyl-4-ethylamino-5-chloro-6-morpholinopyridazinium perchlorate,
1-phenyl-4-methylamino-5-chloro-6-morpholinopyridazinium chloride, 1-phenyl-4-amino-5-chloro-6-pyrrolidinopyridazinium perchlorate,
1-phenyl-4-methylaminopyridazinium perchlorate,
1-phenyl-4-ethylaminopyridazinium perchlorate,
1-phenyl-4-isopropylaminopyridazinium perchlorate,
1-phenyl-4-dimethylaminopyridazinium perchlorate,
1-phenyl-4-dimethylamino-6-ethylmercaptopyridazinium perchlorate and
1-($\beta$-hydroxyethyl)-4,5-dichloro-6-aminopyridazinium perchlorate.

The following compounds are particularly emphasized for their pharmacological effectiveness:

1-phenyl-4-aminopyridazinium perchlorate,
1-(p-chlorophenyl)-4-aminopyridazinium perchlorate,
1-benzyl-4-aminopyridazinium perchlorate,
1-cyclohexyl-4-aminopyridazinium perchlorate,
1-(m-trifluoromethylphenyl)-4-($\beta$-chloroethylamino)-5-chloropyridazinium sulfate,
1-phenyl-4-amino-5-chloropyridazinium sulfate,
1-phenyl-4-amino-6-methylmercaptopyridazinium methosulfate,
1-phenyl-4-amino-6-ethylmercaptopyridazinium hydrogen sulfate,
1-phenyl-4-amino-6-benzylmercaptopyridazinium chloride,
1-phenyl-4-amino-5-chloro-6-anilinopyridazinium chloride,
1-phenyl-4-amino-6-phenoxypyridazinium perchlorate,
1-phenyl-4-amino-6-hydrazinopyridazinium perchlorate,
1-phenyl-4-amino-6-dimethylaminopyridazinium perchlorate,
1-phenyl-4-amino-6-pyrrolidinopyridazinium perchlorate,
1-phenyl-4-amino-6-morpholinopyridazinium perchlorate,
1-phenyl-4-amino-6-piperidinopyridazinium perchlorate and
1-phenyl-4-amino-6-n-butylaminopyridazinium perchlorate.

The parts given in the following Examples are by weight.

EXAMPLE 1

20.3 parts of 1-phenyl-4-amino-6-chloropyridazinium perchlorate, 200 parts of water, 10 parts of sodium bicarbonate and about 5 parts of Raney nickel are stirred for about three hours in an autoclave at 20° to 25°C and a hydrogen pressure of 200 atmospheres gauge. The reaction solution is filtered from catalyst and evaporated. The cyrstalline residue is washed with a little water. 15.6 parts (86.7% of theory) of 1-phenyl-4-aminopyridazinium perchlorate is obtained; $C_{10}H_{10}O_4N_3Cl$, melting point 184° to 186°C after having been recrystallized from methanol.

EXAMPLE 2

The procedure of Example 1 is repeated but using 18 parts of 1-(p-chlorophenyl)-4-amino-6-chloropyridazinium perchlorate. 13.3 parts (82% of theory) of 1-(p-chlorophenyl)-4-aminopyridazinium perchlorate is obtained; $C_{10}H_9O_4N_3Cl_2$, melting point 180° to 182°C after having been recrystallized from methanol.

EXAMPLE 3

The procedure of Example 1 is followed but 8 parts of 1-(p-methylphenyl)-4-methylamino-6-chloropyridazinium perchlorate is used. 6.1 parts (85% of theory) of 1-(p-methylphenyl)-4-methylaminopyridazinium perchlorate is obtained; $C_{12}H_{14}O_4N_3Cl$, melting point 122° to 124°C after having been recrystallized from alcohol.

EXAMPLE 4

15 parts of 1-methyl-3-phenyl-4-methylamino-6-chloropyridazinium perchlorate, 100 parts of water, 5 parts of triethylamine and about 2 parts of Raney nickel are treated at room temperature in a shaking apparatus with hydrogen at atmospheric pressure. After 24 hours the reaction mixture is suction filtered, the residue is boiled with 200 parts of methanol and filtered and the filtrate is concentrated and cooled. 10.3 parts (76.6% of theory) of 1-methyl-3-phenyl-4-methylaminopyridazinium perchlorate is obtained; $C_{12}H_{14}O_4N_3Cl$, melting point 155° to 157°C.

EXAMPLE 5

The procedure of Example 4 is repeated but 13 parts of 1-benzyl-4-amino-6-chloropyridazinium perchlorate is used and 10 parts of sodium bicarbonate is used instead of triethylamine. 9.6 parts (67.3% of theory) of 1-benzyl-4-aminopyridazinium perchlorate is obtained from the filtrate from the reaction mixture; $C_{11}H_{12}O_4N_3Cl$, melting point 127° to 129°C after having been recrystallized from water.

EXAMPLE 6

The procedure of Example 4 is adopted but without triethylamine and 15.6 parts of 1-cyclohexyl-4-amino-6-chloropyridazinium perchlorate is used. 8.6 parts (62.1% of theory) of 1-cyclohexyl-4-aminopyridazinium perchlorate is obtained; $C_{10}H_{16}O_4N_3Cl$, melting point 114° to 116°C after having been recrystallized from water.

EXAMPLE 7

20.5 parts of 1-phenyl-4-aminopyridazinethione-(6) is stirred in 150 parts of glacial acetic acid with 40 parts of a 30% by weight aqueous hydrogen peroxide solution for 4 hours at 110° to 120°C. The glacial acetic acid is then distilled off. 19.6 parts (88% of theory) of 1-phenyl-4-aminopyridazinium sulfate is obtained; $C_{20}H_{20}O_4N_6S$, melting point 187° to 188°C. The perchlorate melts at 184° to 185°C and is identical with the substance from Example 1.

EXAMPLE 8

17.5 parts of 1-methyl-4-amino-5-chloropyridazinethione-(6) is treated with hydrogen peroxide as described in Example 7. 18 parts (92.7% of theory) of 1-methyl-4-amino-5-chloropyridazinium sulfate is obtained; $C_{10}H_{16}O_4N_6SCl_2$, melting point 213° to 214°C.

EXAMPLE 9

9 parts of 1-(m-trifluoromethylphenyl)-4-($\beta$-chloroethylamino)-5-chloropyridazinethione-(6) are treated with 20 parts of hydrogen peroxide as described in Example 7. 8 parts (84.9% of theory) of 1-(m-trifluoromethylphenyl)-4-($\beta$-chloroethylamino)-5- chloropyridazinium sulfate is obtained; $C_{26}H_{22}O_4N_6SCl_1$, melting point 209° to 211°C.

EXAMPLE 10

11.9 parts of 1-phenyl-4-amino-5-chloropyridazinethione-(6) is treated with 10.5 parts of hydrogen peroxide as described in Example 7. 11.2 parts (87.9% of theory) of 1-phenyl-4-amino-5-chloropyridazinium sulfate is obtained; $C_{20}H_{18}O_4N_6SCl_2$, melting point 205° to 206°C after having been recrystallized from alcohol. The chloride melts at 202° to 204°C.

EXAMPLE 11

8 parts of 1-phenyl-5-chloropyridazone-(4) is stirred in 150 parts of toluene with 8 parts of triethyloxonium tetrafluoborate for 3 hours at 80° to 90°C. The oil formed is separated and alcohol is added to it. 8.5 parts (67.9% of theory) of 1-phenyl-4-ethoxy-5-chloropyridazinium tetrafluoborate is obtained; $C_{12}H_{12}ON_2BClF_4$, melting point 188° to 190°C.

EXAMPLE 12

10 parts of 1-phenyl-5-chloropyridazone-(4) in 200 parts of ethylene chloride has 26 parts of oxalyl chloride added to it at room temperature while stirring. 12 parts (94.8% of theory) of 1-phenyl-4,5-dichloropyridazinium chloride is obtained; $C_{10}H_7N_2Cl_3$ (washed with acetone). The substance has a melting point of above 300°C, is easily soluble in water and has a chlorine number of 40.5% (calculated 40.8%).

EXAMPLE 13

10 parts of the betaine of 1-methyl-3-hydroxy-4,5-dichloropyridazinium salt:

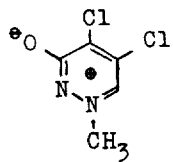

is boiled in 100 parts of thionyl chloride for two hours with an addition of 1 part of dimethylformamide. 9.5 parts (72.7% of theory) of 1-methyl-3,4,5-trichloropyridazinium chloride is obtained; $C_5H_4N_2Cl_4$, washed with acetonitrile.

The substance has a melting point above 300°C, is readily soluble in water and has a chlorine number of 61.4% (calculated: 60.7%).

EXAMPLE 14

20 parts of 1-(β-hydroxyethyl)-4-aminopyridazone-(6) is stirred in 200 parts of alcohol with 20 parts of 70% by weight perchloric acid for 2 hours at 70°C. After the solvent has been evaporated 31 parts (94.2% of theory) of 1-(β-hydroxyethyl)-4-amino-6-hydroxypyridazinium perchlorate is obtained; $C_6H_{10}O_6N_3Cl$, melting point 139° to 140°C (washed with ethyl acetate).

EXAMPLE 15

18.7 parts of 1-phenyl-4-aminopyridazone-(6) in 200 parts of xylene has 10 parts of sulfuric acid added to it and the whole is stirred at 60° to 70°C for thirty minutes. 27 parts (94.7% of theory) of 1-phenyl-4-amino-6-hydroxypyridazinium hydrogen sulfate is obtained; $C_{10}H_{11}O_5N_3S$, melting point 212° to 214°C after having been washed with acetonitrile.

EXAMPLE 16

15 parts of 1-phenyl-4-aminopyridazinethione-(6) is dissolved in 200 parts of a 20% by weight hydrochloric acid while stirring. After a few minutes 16 parts of 1-phenyl-4-amino-6-mercaptopyridazinium chloride crystallizes out (90.4% of theory ($C_{10}H_{10}N_3SCl$; the melting point is 170° to 190°C with decomposition; chlorine number: 15.0% (calculated 14.8%).

EXAMPLE 17

18.7 parts of 1-phenyl-4-aminopyridazone-(6) in 250 parts of xylene is stirred with 24.1 parts of amyl p-toluenesulfonate for 3 hours at 130° to 135°C. The oil thus obtained is intensely mixed with 100 parts of benzene, 100 parts of water and 20 parts of a 70% by weight perchloric acid. After the benzene has been evaporated 14 parts (39.15% of theory) of 1-phenyl-4-amino-6-pentoxypyridazinium perchlorate is obtained; $C_{15}H_{20}O_5N_3Cl$, melting point 118° to 120°C after having been recrystallized from ethyl acetate.

EXAMPLE 18

18.7 parts of 1-phenyl-4-aminopyridazone-(6) in 200 parts of xylene is stirred with 29 parts of octyl p-toluenesulfonate for 3 hours at 130° to 135°C. During cooling 4 parts of starting product crystallizes out. The filtered solution is evaporated and the oily residue is mixed intensely with 100 parts of benzene, 100 parts of water and 20 parts of a 70% by weight perchloric acid. After the benzene has been evaporated an oil is again obtained which crystallizes upon the addition of petroleum ether. 5.5 parts (17.5% of theory) of 1-phenyl-4-amino-6-octoxypyridazinium perchlorate is obtained; $C_{18}H_{26}O_5N_3Cl$, melting point 105° to 106°C after having been washed with petroleum ether.

EXAMPLE 19

20 parts of 1-phenyl-4-amino-6-chloropyridazinium perchlorate in 200 parts of acetonitrile is stirred with 9.4 parts of phenol and 8 parts of pyridine for 3 hours at 80°C. The solvent is evaporated and the oil which remains is mixed well with 100 parts of water and 100 parts of ethyl acetate. After the ethyl acetate phase has been evaporated 11 parts (46.4% of theory) of 1-phenyl-4-amino-6-phenoxypyridazinium perchlorate is obtained; $C_{16}H_{14}O_5N_3Cl$, melting point 174° to 176°C after having been recrystallized from a mixture of ethyl acetate and alcohol.

EXAMPLE 20

24 parts of 1-phenyl-4-amino-5-chloropyridazinethione-(6) in 400 parts of xylene is stirred with 14.2 parts of methyl iodide for 4 hours at 130°C. 35 parts (91.3% of theory) of 1-phenyl-4-amino-5-chloro-6-methylmercaptopyridazinium iodide is obtained; $C_{11}H_{11}N_3SClI$, melting point 184° to 186°C after having been recrystallized from acetonitrile. The methosulfate melts at 124° to 126°C and the perchlorate at 186° to 187°C.

EXAMPLE 21

20.3 parts of 1-phenyl-4-aminopyridazinethione-(6) in 200 parts of toluene is stirred with 20 parts of dimethyl sulfate for 30 minutes at 80° to 90°C. 27.6 parts (83.9% of theory) of 1-phenyl-4-amino-6-methylmercaptopyridazinium methosulfate is obtained; $C_{12}H_{15}O_4N_3S_2$, melting point 130° to 132°C after having been recrystallized from acetonitrile.

EXAMPLE 22

10 parts of 1-phenyl-4-aminopyridazinethione-(6) in 200 parts of toluene is stirred with 8 parts of diethyl sulfate for 4 hours at 80°C. 15 parts of a crude product is obtained which after having been recrystallized from acetone gives 7.5 parts (46.3% of theory) of 1-phenyl-4-amino-6-ethylmercaptopyridazinium hydrogen sulfate: $C_{12}H_{15}O_4N_3S_2$, melting point 195° to 196°C. The formation of the hydrogen sulfate is attributable to the use of diethyl sulfate already partly hydrolyzed. The perchlorate melts at 187° to 188°C.

EXAMPLE 23

20.3 parts of 1-phenyl-4-aminopyridazinethione-(6) in 200 parts of toluene is stirred with 11 parts of β-dimethylaminoethyl chloride for 2 hours at 110°C. The oil thus obtained is dissolved in 150 parts of dilute hydrochloric acid and then 50 parts of 70% by weight perchloric acid is added. 32 parts (67.4% of theory) of 1-phenyl-4-amino-6-(β-dimethylammonium)-ethyl-mercaptopyridazinium diperchlorate is obtained; $C_{14}H_{20}O_8N_4SCl_2$, melting point 215° to 218°C after having been recyrstallized from water.

EXAMPLE 24

24.4 parts of 1-methyl-4-amino-6-chloropyridazinium perchlorate in 250 parts of acetonitrile is stirred with 10 parts of ethylmercaptan and 10 parts of triethylamine for four hours at 50° to 60°C. After the solvent has been distilled off the residue is washed with 100 parts of water. 18.3 parts (67.9% of theory) of 1-methyl-4-amino-6-ethylmercaptopyridazinium perchlorate is obtained; $C_7H_{12}O_4N_3SCl$, melting point 136° to 137°C after having been recrystallized from alcohol.

EXAMPLE 25

37.1 parts of 1-phenyl-4-ammonium-6-chloropyridazinium diperchlorate in 200 parts of acetonitrile is stirred with 20.2 parts of laurylmercaptan. Within thirty minutes 10 parts of triethylamine is added and the whole is stirred for 2 hours at 80°C. After the solvent has been distilled off and the residue has been treated with 100 parts of water 32 parts (74.5% of theory) of 1-phenyl-4-amino-6-dodecylmercaptan-pyridazinium perchloride is obtained; $C_{22}H_{34}O_4N_3SCl$, melting point 95° to 97°C after having been recrystallized from cyclohexane.

EXAMPLE 26

37 parts of 1-phenyl-4-ammonium-6-chloropyridazinium diperchlorate in 200 parts of acetonitrile is stirred with 11 parts of thiophenol and 8 parts of pyridine for 2 hours at 80°C. After the acetonitrile has been distilled off and the residue has been treated with 100 parts of water 30.5 parts (93.4% of theory) of 1-phenyl-4-amino-6-phenylmercaptopyridazinium perchlorate is obtained; $C_{16}H_{14}O_4N_3SCl$, melting point 180° to 183°C after having been recrystallized from alcohol.

EXAMPLE 27

28 parts of 1-phenyl-4-amino-6-chloropyridazinium chloride in 200 parts of acetonitrile is stirred with 18 parts of β,γ,γ-trichloroallylmercaptan and 10 parts of triethylamine for 2 hours at 80°C. After cooling the whole is suction filtered and after the residue has been recrystallized from methanol 22 parts (49.7% of theory) of 1-phenyl-4-amino-6-(β,γ,γ-trichloroallylmercapto)-pyridazinium chloride is obtained; $C_{13}H_{11}N_3SCl_4$, melting point 96° to 100°C.

EXAMPLE 28

5 parts of 1-phenyl-4-amino-6-mercaptopyridazinium chloride in 100 parts of toluene is stirred with 2.5 parts of benzyl chloride for 1 hour at 110°C. 6.2 parts (90.2% of theory) of 1-phenyl-4-amino-6-benzylmercaptopyridazinium chloride is obtained; $C_{17}H_{16}N_3SCl$, melting point 226° to 228°C after having been recrystallized from alcohol. The perchlorate melts at 170° to 171°C.

EXAMPLE 29

15 parts of 1-phenyl-4-amino-5,6-dichloropyridazinium chloride is slowly introduced into a melt of 50 parts of urea (temperature about 130°C). After fifteen minutes the melt is cooled and 150 parts of a 10% by weight caustic soda solution is added. A crystalline substance separates out (melting point 180° to 181°C after having been recrystallized from acetonitrile) which is dissolved in 50 parts of concentrated hydrochloric acid. The hydrochloric acid solution is evaporated and the oil which remains is caused to crystallize with a mixture of butyl acetate and alcohol. 11.5 parts (82.5% of theory) of 1-phenyl-4-amino-5-chloro-6-aminopyridazinium chloride is obtained; $C_{10}H_{10}N_4Cl_2$. The substance melts at above 300°C. The chlorine number is 27.9% (calculated 27.65%). The perchlorate melts at 160° to 163°C.

EXAMPLE 30

30 parts of 1-phenyl-4-amino-5,6-dichloropyridazinium chloride in 150 parts of water is stirred with 18 parts of aniline for 10 minutes at 50°C. The solution has 50 parts of concentrated hydrochloric acid added to it and is cooled to 10°C. 30.5 parts (84.6% of theory) of 1-phenyl-4-amino-5-chloro-6-anilinopyridazinium chloride is obtained; $C_{16}H_{14}N_4Cl_2$, melting point (with decomposition) 130°C after having been recrystallized from water.

EXAMPLE 31

22 parts of 1-methyl-4,5,6-trichloropyridazinium hexachlorophosphate is stirred in 150 parts of benzene. Within thirty minutes a solution of 9 parts of aniline in 50 parts of benzene is dripped in and the mixture is kept at 80°C for an hour. After cooling 19.7 parts (87.8% of theory) of 1-methyl-4,5-dichloro-6-anilinopyridazinium chloride are suction filtered; $C_{11}H_{10}N_3Cl_3$, melting point (with decomposition) 215°C after having been recrystallized from acetonitrile.

EXAMPLE 32

9.2 parts of methylhydrazine is dripped into 40 parts of 1-phenyl-4-amino-6-chloropyridazinium perchlorate in 250 parts of acetonitrile. The mixture is stirred for 1 hour at 80°C. After the acetonitrile has been distilled off the oily residue has 50 parts of water added to it. 31 parts (75.3% of theory) of 1-phenyl-4-amino-6-(α-methylhydrazino)-pyridazinium perchlorate is obtained; $C_{11}H_{14}O_4N_5Cl$, melting point 147° to 148°C after having been recrystallized from alcohol.

EXAMPLE 33

32 parts of 1-phenyl-4,6-diamino-5-chloropyridazinium perchlorate in 200 parts of water in a stirred autoclave is stirred with 10 parts of sodium bicarbonate and 2 parts of Raney nickel for 3 hours at 100°C and 200 atmospheres gauge of hydrogen pressure. The discharge is filtered free from nickel and 20 parts of a 70% by weight perchloric acid is added to it. 22 parts (76.8% of theory) of 1-phenyl-4,6-diaminopyridazinium perchlorate is obtained; $C_{10}H_{11}O_4N_4Cl$, melting point 105° to 107°C after having been recrystallized from water.

EXAMPLE 34

20 parts of 1-phenyl-4-amino-5-chloropyridazinethione-(6) is heated in 100 parts of dimethyl sulfate to 120°C while stirring. After 10 minutes the reaction mixture is cooled. 2 parts (3% of theory) of 1-phenyl-4-amino-5-chloro-6-methylmercaptopyridazinium methosulfate crystallizes out; $C_{12}H_{14}O_4N_3S_2Cl$, melting point 124° to 126°C; identical with the methosulfate from Example 20. The filtrate is concentrated at subatmospheric pressure and the residue is dissolved in about 200 parts of water and by adding 9 parts of a 70% by weight perchloric acid 26 parts (87.7% of theory) of 1-phenyl-4-amino-5-chloro-6-methylmercaptopyridazinium perchlorate is precipitated; $C_{11}H_{11}O_4N_3SCl_2$, melting point 186° to 187°C; identical with the substance from Example 20.

EXAMPLE 35

15.3 parts of 1-phenyl-4-amino-6-chloropyridazinium perchlorate is dissolved in 200 parts of water at 80° to 90°C; 5 parts of hydrazine hydrate is added and the whole is boiled for 3 hours. The reaction solution is concentrated to about half its volume and cooled. 13 parts (81.3% of theory, as hydrate) of 1-phenyl-4-amino-6-hydrazinopyridazinium perchlorate is obtained; $C_{10}H_{12}O_4N_5Cl.H_2O$, obtained with 1 mole of water of crystallization when recrystallized from water. Melting point 63° to 65°C.

EXAMPLE 36

As described in Example 35 16 parts (88% of theory) of 1-methyl-4-amino-6-hydrazinopyridazinium perchlorate $C_5H_{10}O_4N_5Cl$, melting point 227° to 229°C with decomposition after having been recrystallized from water, is obtained from 18.5 parts of 1-methyl-4-amino-6-chloropyridazinium perchlorate and 7.5 parts of hydrazine hydrate.

EXAMPLE 37

18 parts of 1-methyl-4-amino-6-chloropyridazinium perchlorate is dissolved in 200 parts of water at 80° to 90°C. 10 parts of a 25% by weight aqueous ammonia solution is added and the whole is boiled for two hours. After cooling and filtration 11 parts (66.5% of theory) of 1-methyl-4,6-diaminopyridazinium perchlorate, $C_5H_9O_4N_4Cl$, melting point 181° to 183°C after having been recrystallized from water is obtained.

EXAMPLE 38

24.4 parts of 1-methyl-4-amino-6-chloropyridazinium perchlorate in 200 parts of acetonitrile is stirred with 12.4 parts of benzylmercaptan and 20 parts of triethylamine for 3 hours at 80°C. The solvent is then distilled off at subatmospheric pressure, the residue is treated with about 300 parts of water and the sparingly soluble reaction product is suction filtered. 29.5 parts (89.2% of theory) of 1-methyl-4-amino-6-benzylmercaptopyridazinium perchlorate is obtained; $C_{12}H_{14}O_4N_3SCl$, melting point 139° to 141°C.

EXAMPLE 39

12.2 parts of 1-methyl-4-amino-6-chloropyridazinium perchlorate in 150 parts of acetonitrile is stirred with 5 parts of phenol and 4 parts of pyridine for 4 hours at 80°C. The reaction mixture is filtered and the filtrate is concentrated at subatmospheric pressure. About 200 parts of water is added. 5.5 parts (36.6% of theory) of 1-methyl-4-amino-6-phenoxypyridazinium perchlorate is obtained; $C_{11}H_{12}O_5N_3Cl$, melting point 182° to 184°C after having been recrystallized from water.

EXAMPLE 40

12.2 parts of 1-phenyl-4-amino-6-methoxypyridazinium methosulfate in 100 parts of a 40% by weight aqueous dimethylamine solution is stirred for 1 hour at 80° to 90°C. The excess amine is distilled off and the reaction solution is acidified with hydrochloric acid. 20 parts of a 70% by weight aqueous perchloric acid is added and 8 parts (80.4% of theory) of 1-phenyl-4-amino-6-dimethylaminopyridazinium perchlorate crystallizes out; $C_{12}H_{16}O_4N_4Cl$, melting point 177° to 178°C after having been recrystallized from water.

EXAMPLE 41

15.3 parts of 1-phenyl-4-amino-6-chloropyridazinium perchlorate is dissolved in 250 parts of water at 80° to 90°C. 9.3 parts of aniline is added and the whole is stirred for 1 hour at 95° to 100°C. AFter cooling 12 parts (66.4% of theory) of 1-phenyl-4-amino-6-anilinopyridazinium perchlorate is obtained, $C_{16}H_{15}O_4N_4Cl$, melting point 164° to 166°C after having been recrystallized from water.

EXAMPLE 42

9 parts (47.8% of theory) of 1-phenyl-4-amino-6-benzylaminopyridazinium perchlorate, $C_{17}H_{17}O_4N_4Cl$, melting point 100° to 102°C is obtained with 10.7 parts of benzylamine analogously to Example 41.

EXAMPLE 43

12.5 parts (73.5% of theory) of 1-phenyl-4-amino-6-pyrrolidinopyridazinium perchlorate, $C_{14}H_{17}O_4N_4Cl$, melting point 209° to 211°C after having been recrystallized from water is obtained with 7.1 parts of pyrrolidine by a process analogous to that described in Example 41.

EXAMPLE 44

By the method described in Example 41 there is obtained with 8.7 parts of morpholine 10 parts (56.3% of theory) of 1-phenyl-4-amino-6-morpholinopyridazinium perchlorate, $C_{14}H_{17}O_5N_4Cl$, melting point 150° to 152°C after having been recrystallized from water.

EXAMPLE 45

12 parts (67.8% of theory) of 1-phenyl-4-amino-6-piperidinopyridazinium perchlorate, $C_{15}H_{19}O_4N_4Cl$, melting point 137° to 139°C after having been recrystallized from water is obtained as described in Example 41 with 8.5 parts of piperidine.

EXAMPLE 46

9 parts (52.7% of theory) of 1-phenyl-4-amino-6-n-butylaminopyridazinium perchlorate, $C_{14}H_{19}O_4N_4Cl$, melting point 150° to 152°C after having been recrystallized from a mixture (1:1) of water and methanol is obtained analogously to Example 41 with 5.5 parts of n-butylamine.

EXAMPLE 47

8 parts (41% of theory) of 1-phenyl-4-amino-6-(β-phenylethyl)-aminopyridazinium perchlorate, $C_{18}H_{19}O_4N_4Cl$, melting point 209° to 211°C is obtained by an analogous method to that described in Example 41 with 9.1 parts of β-phenylethylamine.

We claim:
1. A pyridazinium compound of the formula:

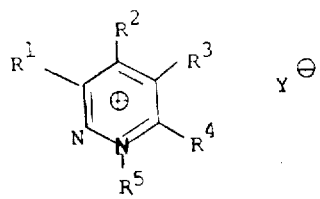

in which
R¹ is hydrogen;
R² is amino;
R³ is hydrogen;
R⁴ is

in which both radicals R⁷ are methyl or are together with the nitrogen pyrrolidino;
R⁵ is phenyl; and,
Y⁻ is a pharmaceutically acceptable anion of an inorganic or organic acid selected from the group consisting of perchloric acid, hydrochloric acid, hydrobromic acid, hydroiodic acid, phosphoric acid, carbonic acid, sulfuric acid, methylsulfuric acid, ethylsulfuric acid, trifluoromethylsulfonic acid, nitric acid or fluoboric acid, formic acid, acetic acid, trifluoroacetic acid, propionic acid, glycolic acid, lactic acid, pyruvic acid, oxalic acid, malonic acid, succinic acid, maleic acid, fumaric acid, malic acid, tartaric acid, citric acid, ascorbic acid, benzoic acid, phenylacetic acid, 4-amino-benzoic acid, 4-hydroxybenzoic acid, anthranilic acid, cinnamic acid, mandelic acid, salicylic acid, 4-aminosalicylic acid, 2-acetoxysalicylic acid, p-toluenesulfonic acid, isonicotinic acid, nicotinic acid, methionine, tryptophan, lysine and arginine.

2. 1-phenyl-4-amino-6-dimethylaminopyridazinium perchlorate.

3. 1-phenyl-4-amino-6-pyrrolidinopyridazinium perchlorate.

* * * * *